United States Patent [19]

Wilkinson et al.

[11] Patent Number: 4,786,279

[45] Date of Patent: Nov. 22, 1988

[54] CONTAINER FOR MIXTURE OF MATERIALS

[75] Inventors: Kenneth E. Wilkinson, Round Lake; Kenneth H. Knox, Vernon Hills; Marc T. Hedlund, Gurnee; Mark E. Larkin, Lindenhurst, all of Ill.

[73] Assignee: Abbott Laboratories, North Chicago, Ill.

[21] Appl. No.: 891,099

[22] Filed: Jul. 31, 1986

[51] Int. Cl.[4] .............................................. A61M 5/14

[52] U.S. Cl. ..................................... 604/88; 604/411; 604/415

[58] Field of Search ................. 604/56, 80, 82, 86-88, 604/191, 262, 408, 410, 411, 415, 416, 414; 222/81, 85

[56] References Cited

U.S. PATENT DOCUMENTS

| | | | |
|---|---|---|---|
| 605,178 | 6/1898 | Ferguson | 604/80 |
| 2,176,923 | 10/1939 | Nitardy . | |
| 2,590,900 | 4/1952 | Sommerstein . | |
| 2,721,552 | 11/1955 | Nosik . | |
| 2,758,597 | 8/1956 | Elder | 604/80 |
| 2,778,360 | 1/1957 | Miskel . | |
| 3,064,652 | 11/1962 | Corcoran et al. | 604/408 |
| 3,290,017 | 12/1966 | Davies . | |
| 3,306,563 | 2/1967 | Soto . | |
| 3,532,254 | 10/1970 | Burke . | |
| 3,636,950 | 1/1972 | Gomez . | |
| 3,840,136 | 10/1974 | Lanfranconi et al. . | |
| 3,875,012 | 4/1975 | Dorn et al. . | |
| 3,915,212 | 10/1975 | Bujan et al. . | |
| 3,968,872 | 7/1976 | Cavazza . | |
| 4,000,740 | 1/1977 | Mittleman | 604/86 |
| 4,044,757 | 8/1977 | McWhorter et al. | 604/82 |
| 4,048,999 | 9/1977 | Kobel . | |
| 4,059,112 | 11/1977 | Tischlinger . | |
| 4,089,325 | 5/1978 | Crankshaw et al. . | |
| 4,161,178 | 4/1979 | Genese . | |
| 4,161,949 | 7/1979 | Thanawalla | 604/411 |
| 4,172,457 | 10/1979 | Choksi et al. . | |
| 4,177,893 | 2/1980 | Bujan . | |
| 4,289,648 | 9/1981 | Hoskins et al. . | |
| 4,294,351 | 10/1981 | Cheetham . | |
| 4,306,554 | 12/1981 | Schwartz et al. . | |
| 4,392,850 | 7/1983 | Elias et al. . | |
| 4,397,442 | 8/1983 | Larkin . | |
| 4,405,317 | 9/1983 | Case . | |
| 4,412,836 | 11/1983 | Brignola . | |
| 4,417,890 | 11/1983 | Dennehey et al. . | |
| 4,467,588 | 8/1984 | Carveth . | |
| 4,515,586 | 5/1985 | Mendenhall et al. . | |

FOREIGN PATENT DOCUMENTS

| | | |
|---|---|---|
| 0077604 | 4/1983 | European Pat. Off. . |

*Primary Examiner*—Dalton L. Truluck
*Assistant Examiner*—Frank Wilkens
*Attorney, Agent, or Firm*—Michael J. Roth; Martin L. Katz

[57] ABSTRACT

A container having two compartments for keeping two materials in separated relation. When it is desired that the two materials be intermixed, an actuator carrying a pair of piercing pins is inserted into ports of the compartments until membranes blocking exit of the materials from their respective compartment are punctured. When these membranes are punctured the materials are received at a mixing chamber where the materials are mixed.

12 Claims, 1 Drawing Sheet

CONTAINER FOR MIXTURE OF MATERIALS

BACKGROUND OF THE INVENTION

This invention relates to containers which hold two different materials in separated relation prior to mixing. The invention particularly relates to containers for storing liquids separately for subsequent mixing.

In the past, it has been a common practice when mixing two liquids for intravenous administration to connect the two separate containers containing the two liquids by a "Y" connector to tubing leading to a cannula inserted in the patient. There are several problems with such an arrangement.

First, when the containers are made of flexible material (i.e., when they are "I.V. bags"), the walls of one of the flexible bags can stick together for short periods, interfering with the flow of material from that container. Thus, for short periods of time, the mixture at the "Y" connection becomes rich in the material from the other bag, so that a "spike" in the concentration of the other material results in the solution delivered to the patient. These spikes are undesirable, of course.

Another problem with the "Y" connector improper diluent because virtually any two flexible containers can be joined with a "Y" connector if appropriate tubing connectors, piercing pins, and the like, are used. This creates the possibility of inadvertent, improper medicament/diluent mixing.

Another practice is for hospital pharmacies to purchase a container partially filled with one product. A second product is then introduced into the container by pumping or gravity filling, and the two products are mixed. This procedure creates an opportunity for improper medicament/diluent mixing, and it is time consuming.

SUMMARY OF THE INVENTION

The present invention is a container having two compartments, each compartment having a port. The two compartment ports are adjacent each other. A mixing chamber having two inlet ports is also included. Each mixing chamber port is connectible to one of the compartment ports. The mixing chamber further includes an outlet port.

With this arrangement, the inlet ports of the mixing chamber can be simultaneously plugged into or connected with the compartment ports, making the system easy to operate. Furthermore, since the two compartments are in the same container, mixing a medication with the improper diluent is prevented because the medication can be pre-packaged with the proper diluent. Finally, the mixing chamber smooths out spikes in concentration due to intermittent flow reductions or stoppages from one compartment or the other.

BRIEF DESCRIPTION OF THE DRAWINGS

An exemplary embodiment of the invention summarized above is shown in the accompanying drawings wherein.

DETAILED DESCRIPTION OF AN EXEMPLARY EMBODIMENT OF THE INVENTION

Figure 1:
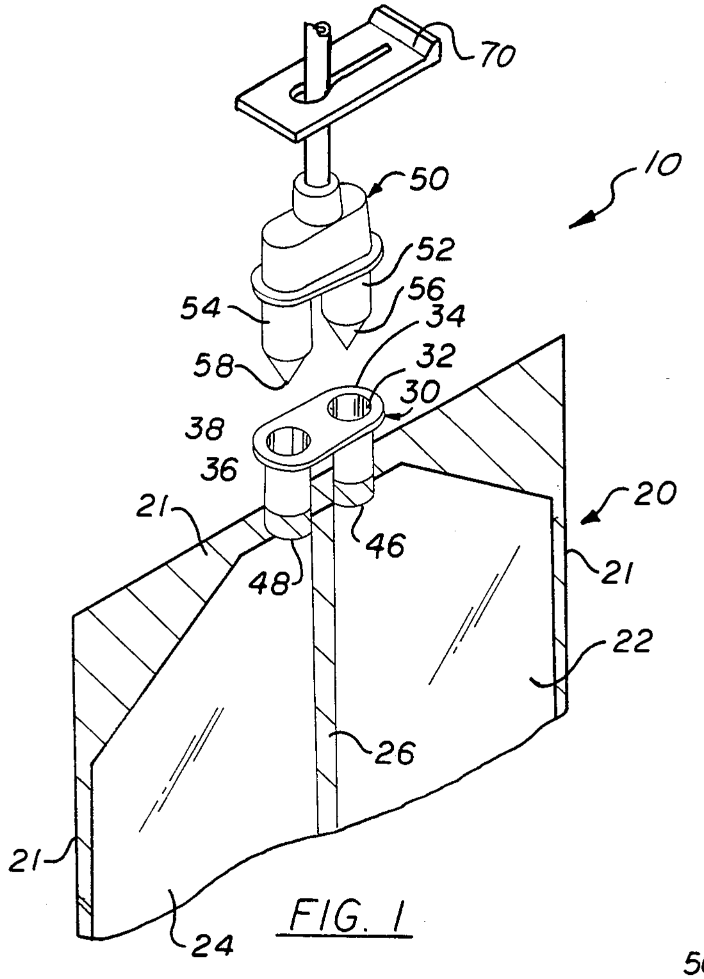
FIG. 1 is a schematic rendering, taken in perspective, of a container illustrative of the invention.

Container 10 of the present invention includes a bag 20 having a first compartment 22 and an adjacent second compartment 24 separated from compartment 22 by mid-seal 26. Bag 20 is formed of two sheets of plastic flexible material heat sealed together along their peripheral edges 21 and in mid-seal area 26. Compartment 22 is adapted to hold a first material (not shown), and compartment 24 is adapted to hold a second, different material (not shown) in separated relation from the first material. Compartment 22 has a first port 46, and compartment 24 has an adjacent, second port 48 separated from port 46 by mid-seal 26. Ports 46 and 48 are mandrel sealed to edge 21 of bag 20.

A support plate 30 has a first recessed, cup shaped member 32 inserted into the first port 46, and a second recessed member 36 inserted into the second port 48. First recessed member 32 defines a first outlet 34, and second recessed member 36 defines a second outlet 38. In this exemplary embodiment, recessed member 32 is adjacent to, and extends parallel with, recessed member 36. The two recessed members are sealed within the compartment ports by welding, adhesives or the like. The bottom of recessed member 32 blocks the path between the first port 46 and the first outlet 34 forming a first pierceable impermeable membrane 42. The bottom of port 48 and the second outlet 38, forming a second pierceable impermeable membrane 44. Support plate assembly 30 not only forms two pierceable membranes to close ports 46 and 48 but it also serves to space the two ports from each other for receiving the piercing pins described below.

A mixing chamber housing 50 includes a first piercing pin or inlet port 52 and a second piercing pin or inlet port 54, preferably extending parallel to each other. Piercing pins 52 and 54 are preferably of substantially circular cross-section each terminating in a sharpened ends 53 and 55 respectively. Piercing pins 52 and 54 are of hollow construction, and thus define internal ducts, 56 and 58, each extending the entire lengths of their respective piercing pins. Internal ducts 56 and 58 terminate in a mixing chamber 60, which has an opening 62 through which a mixture of the contents of compartments 22 and 24 may pass.

In this preferred embodiment, the outside diameter of piercing pins 56 and 58 is preferably substantially the same as the inside diameters of outlets 34 and 38 so that when piercing pins 56 and 58 are inserted therein, they form an interference fit.

In operation, a first material is placed in compartment 22 and a second material is placed in compartment 24. Because compartments 22 and 24 are separated from each other by mid-seal 26, the two materials are stored separately until mixing is desired To mix the materials from compartments 22 and 24, piercing pins 52 and 54 are urged into channels 32 and 36, respectively, to pierce membranes 42 and 44. As can be seen, piercing pins 52 and 54, because they are carried on the same structure, can be pushed into recessed members 32 and 36 simultaneously in one linear motion by hand, simply by aligning piercing pins 52 and 54 with recessed members 32 and 36 and pushing.

Figure 2:
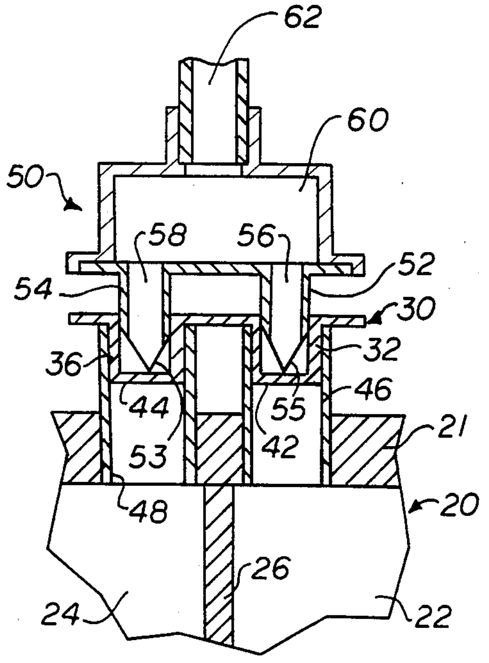
FIG. 2 is an enlarged sectional view of a portion of the container shown in FIG. 1.

To dispense the contents, the container system is inverted from the position shown in FIGS. 1 and 2 to allow the mixture to flow by gravity through opening 62 into the tube(s) connected to the patient. Thus, a path is established between compartments 22 and 24, and mixing chamber 60. In particular, the material in chamber 22 moves into mixing chamber 60 via port 46, recessed member 32, and the internal duct 56 associated with piercing pin 52. Similarly, the material in compartment 24 moves into mixing chamber 60 via port 48, channel 36 and the internal duct 58 associated with piercing pin 54. The two materials are mixed in chamber 60, and are dispensed from mixing chamber 60 via opening 62 once a clamp 70 is released.

As indicated previously, the container system described is primarily useful in dispensing and mixing liquids. Where one liquid is substantially more viscous than the other, it may be necessary to design the port and the piercing pin for the compartment containing the viscous material with wider fluid passageways than the other port and pin. The wider passageway would allow the viscous fluid to flow at a rate equal to the rate of the less viscous fluid. If wider passageways were not provided, the less viscous material would flow out faster, making the I.V. solution more concentrated in the less viscous liquid initially, and less concentrated in the less viscous liquid as more of the mixed product is dispensed. The sizing the passageways for particular combinations of liquids can be designed with routine experimentation.

Figure 3:
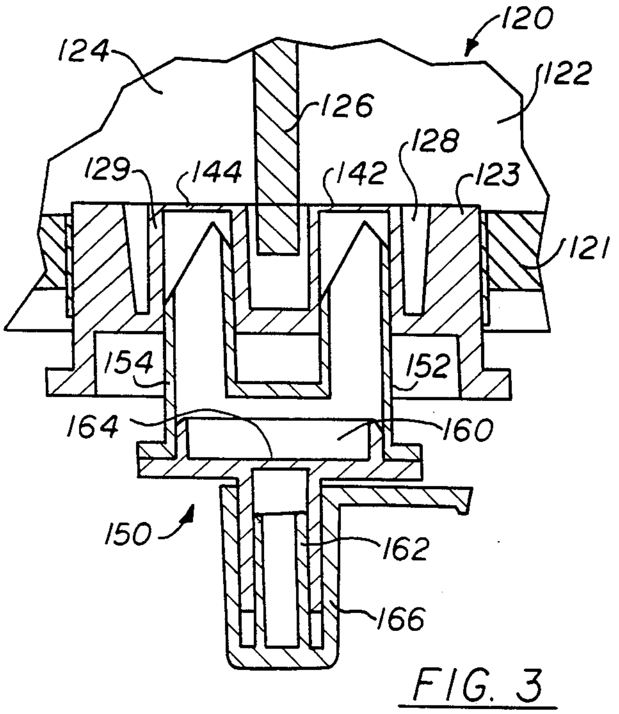
FIG. 3 is an enlarged sectional view of a modified version of the device shown in FIGS. 1 and 2, shown in an inverted position.

A modified embodiment of the container system of the present invention is shown in FIG. 3. It includes a bag 120 substantially the same as bag 20 of FIGS. 1 and 2 being made of two flexible sheets heat sealed together along their peripheral edges 121 with a mid-seal 126 dividing bag 120 into two compartments 122 and 124.

Instead of two separate ports mandrel sealed to edge 121 of bag 120, an integrally molded compartment port assembly 123 is mandrel sealed to edge 121. Port assembly 123 includes two recessed ports 128 and 129 which are closed by pierceable membranes 142 and 144 integrally formed with port seal assembly 123. Ports 123 and 129 are separated from each other by midseal 126. Mixing chamber housing assembly 150 includes two piercing pins 152, 154 adapted to be received within ports 128 and 129, respectively. Housing assembly 150 includes a mixing chamber 160 having an outlet port 162. An integrally formed pierceable membrane 164 extends across port 162. In operation, housing assembly 150 can be urged toward port assembly 123 so that piercing pins 152 and 154 enter ports 128 and 129 and pierce membranes 142 and 144.

The first material in compartment 122 can be mixed with the second material in compartment 124 by manipulating and squeezing the flexible compartments so that material is repeatedly exchanged between them through ports 128, 129, piercing pins 152, 154, and mixing chamber 160.

When the two materials are completely mixed, a protective cap 166 over port 162 is removed, and membrane 164 is pierced with a tubular spike (not shown) attached to a tube (not shown) leading to the patient. This obviates having to "size" the piercing pins, inside diameters to account for any viscosity differences between the two materials in the compartments.

The components of the present invention can be made inexpensively from polymeric materials. The compartmental bags can be made of polyvinyl chloride. The compartment ports, the support plate assembly, the mixing chamber and/or compartment port assembly can be made of any number of medical grade plastics.

In view of the foregoing, it should be apparent that the container of the invention permits mixing of different materials without any special tools or facilities, and without any special operator training Because the two compartments are in the same container, inadvertent mixing of the medicament with an improper diluent is eliminated.

Though the exemplary embodiments of the container herein disclosed are preferred, other embodiments which do not part from the true scope of the invention will be apparent to those skilled in the art. All such embodiments are intended to be covered by the appended claims.

We claim:

1. A container system for mixing two materials, comprising:

a container including first and second compartments;

said first compartment adapted to hold a first material, said first compartment having a first port;

said second compartment adapted to hold a second material, said second compartment having a second port adjacent said first port; and mixing chamber means having two inlet ports, an outlet and a mixing chamber, each mixing chamber port being connectable to one of said compartment ports;

said mixing chamber comprising a single structure carrying both of said inlet ports and holding said inlet ports in spaced relationship to each other corresponding in distance to the distance between the two compartment ports;

said mixing chamber ports comprising piercing pins with passages therethrough, and wherein said first and second compartment ports include pierceable membranes to be pierced by said piercing pins;

whereby said inlet ports can be simultaneously connected to said first and second compartment ports, allowing the materials to flow from said compartment, mix in said mixing chamber, and emerge in a mixed condition from said mixing chamber outlet.

2. The container system as defined on claim 1 wherein said container includes support plate means extending between and holding said first and second compartment ports in spaced relationship to each other corresponding in distance to the distance between said two inlet ports.

3. The container system as recited in claim 2 wherein said support plate means includes two spaced recessed members, each of said recessed members being received within one of said first and second compartment ports, forming pierceable sealing members.

4. The container system as recited in claim 3 wherein said mixing chamber ports comprise piercing pins to pierce said pierceable sealing members.

5. The container system as recited in claim 4 wherein said container is formed from two sheets of plastic material sealed together around their peripheries, and said compartments are formed by an intermediate seal between said sheets dividing said container into two compartments sealed from each other.

6. The container system for mixing two materials as recited in claim 1 wherein said container is formed from two sheets of plastic material sealed together around their peripheries, and said compartments are formed by an intermediate seal between said sheets dividing said container into two compartments sealed from each other.

7. The container system defined in claim 1 wherein the outside dimensions of said piercing pins are substantially the same as the inside dimensions of said ports into which they are to be inserted.

8. The container system as recited in claim 1 pierceable membrane disposed across said outlet whereby the two materials can be mixed in said compartments, and dispensed through said outlet when said membrane is pierced.

9. The container system as recited in claim 1 wherein said first and second chamber ports are integrally formed in a compartment port assembly.

10. A method for mixing two materials, initially maintained in a separated relation, comprising the steps of:

(a) providing a container having a first chamber adapted to hold a first material, a second chamber, isolated from the first chamber, adapted to hold a second material, a first channel communicable with said first chamber and a second channel communicable with said second chamber, communication between each of said first and second channels and their respective chambers being initially blocked by an impermeable membrane;

(b) inserting first and second piercing pins into said first and second channels, respectively, to puncture said impermeable membranes blocking said passage, said piercing pins being carried on a single structure forming a mixing chamber communicating with both of said piercing pins, said structure holding said piercing pins in spaced relationship to each other corresponding in distance to the distance between the first and second channels;

(c) passing said first material from said first chamber through an internal duct in said first piercing pin and into said mixing chamber, and passing said second material from said second chamber through an internal duct in said second piercing pin and into said mixing chamber; and (d) permitting said first and second materials to mix in said mixing chamber.

11. The method defined in claim 10 wherein said piercing pins are inserted into their respective chambers simultaneously.

12. The method defined in claim 10 wherein, after said first and second materials are mixed, they are dispensed from said mixing chamber.

* * * * *

UNITED STATES PATENT AND TRADEMARK OFFICE
CERTIFICATE OF CORRECTION

PATENT NO. : 4,786,279

DATED : November 22, 1988

INVENTOR(S) : Kenneth E. Wilkinson, Kenneth H. Knox, Marc T. Hedlund, Mark E. Larkin It is certified that error appears in the above—identified patent and that said Letters Patent is hereby corrected as shown below:

Column 5, line 5: After "Claim 1" and before "pierceable" insert --wherein said mixing chamber means further includes a--

Signed and Sealed this

Twenty-seventh Day of June, 1989

*Attest:*

DONALD J. QUIGG

*Attesting Officer*

*Commissioner of Patents and Trademarks*